United States Patent
Meyer

(10) Patent No.: US 8,790,671 B2
(45) Date of Patent: Jul. 29, 2014

(54) TOPICAL FUNGICIDAL AGENTS FOR TREATING NAIL DISORDERS

(75) Inventor: Hans Meyer, Riehen/BS (CH)

(73) Assignee: Bioequal AG, Muttenz/BL (CH)

( * ) Notice: Subject to any disclaimer, the term of this patent is extended or adjusted under 35 U.S.C. 154(b) by 25 days.

(21) Appl. No.: 12/450,552

(22) PCT Filed: Apr. 3, 2008

(86) PCT No.: PCT/EP2008/002642
§ 371 (c)(1),
(2), (4) Date: Oct. 30, 2009

(87) PCT Pub. No.: WO2008/128627
PCT Pub. Date: Oct. 30, 2008

(65) Prior Publication Data
US 2010/0113593 A1    May 6, 2010

(30) Foreign Application Priority Data
Apr. 20, 2007   (CH) ........................ 656/07

(51) Int. Cl.
*A01N 25/34*    (2006.01)

(52) U.S. Cl.
USPC ............... 424/404; 424/61; 514/68

(58) Field of Classification Search
USPC ........................ 424/404, 61; 514/68
See application file for complete search history.

(56) References Cited

U.S. PATENT DOCUMENTS

| | | | |
|---|---|---|---|
| 6,740,326 B1 * | 5/2004 | Meyer et al. ............ | 424/401 |
| 7,524,122 B2 * | 4/2009 | Pink ...................... | 401/129 |
| 2005/0020678 A1 * | 1/2005 | Denton ................. | 514/546 |

* cited by examiner

*Primary Examiner* — Lezah Roberts
*Assistant Examiner* — Nannette Holloman
(74) *Attorney, Agent, or Firm* — Wenderoth, Lind & Ponack, L.L.P.

(57) ABSTRACT

Anhydrous agents for topical application, comprising one or more C1-C4 alkyl esters of lactic acid, malic acid, tartaric acid or citric acid and physiologically acceptable excipients, are described for the treatment of nail disorders caused by mycoses and for nail care. The agents according to the invention are also suitable in veterinary medicine for treating fungal infections of the hooves, claws and talons of pets and farm animals and wild animals living in captivity.

10 Claims, No Drawings

TOPICAL FUNGICIDAL AGENTS FOR TREATING NAIL DISORDERS

This application is a U.S. national stage of International Application No. PCT/EP2008/002642 filed Apr. 3, 2008.

This invention relates to anhydrous, topical agents which are intended for the treatment of nail disorders caused by mycoses and for nail care and which contain a C1-C4 alkyl ester of lactic acid, malic acid, tartaric acid or citric acid and, where applicable, physiologically acceptable excipients.

The invention also relates to use of the fungicidal agent in any form of administration.

The application PCT/CH 99/0049 describes topical agents comprising one or more active substances in addition to carriers, including acid esters and, where applicable, physiologically acceptable excipients.

Surprisingly, it was found that agents comprising only one C1-C4 alkyl ester of lactic acid, malic acid, tartaric acid or citric acid or mixtures thereof without further additives are outstandingly suitable for the treatment of nail disorders caused by a mycotic infection (fungal infection).

Surprisingly, these topical antimycotic agents can be used extremely effectively without the addition of further active substances and without the addition of further carriers.

The bactericidal effect of C1-C4 alkyl esters of lactic acid, malic acid, tartaric acid and citric acid is sufficiently known in the prior art.

In GBP 1234297, for example, the fungicidal effect of low-alkyl esters lactic acid, malic acid, tartaric acid and citric acid is neither described nor mentioned in combination with other active substances. The various lactic acid esters are also not mentioned as bactericidal agents.

In U.S. Pat. No. 3,806,513, lactic acid esters with low alkanols as carriers are described as effective for the treatment of acne, pityriasis and oleosa capitis. The fungicidal or antimycotic effect is not mentioned, only the bactericidal effect. The esters are used in combination with alcohols in alcoholic solution as carriers.

In GBP 156 1475, the manufacture of bacteriostatic solutions is described as capable of being used as a deodorant, the free lactic acid being in alcoholic solution. Lactic acid esters are not mentioned, but the hydrolysation of these esters is. It has to be concluded that there is an equilibrium. A fungicidal effect of the solutions is not described. The suspicion is expressed that part of the bactericidal effect is attributable to the alcohol used.

U.S. 2005019355 describes compositions that reduce bacteria on the hand, comprise esters of lactic acid and are bacteriostatically effective in particular. The esters of lactic acid are dissolved in various solvents. A fungicidal effect is by no means described or even claimed.

WO 2004032886 describes the use of lactic and citric acid salts as bactericidal agents. In particular, it describes the use of these agents on the skin and in particular for the hair to combat bacteria. Fungicidal effects are neither mentioned nor claimed. The use of surfactants (surface active agents) and in particular the use of a second acid is described as advantageous.

In none of the patent specifications mentioned is reference made to the fungicidal effect of the esters of lactic, malic, tartaric or citric acid, which are suitable for the treatment of diseases of the nail bed resulting from fungal infection.

Surprisingly, the C1-C4 alkyl esters can be used as fungicidal active substances and at the same time also as carriers, if needed, which make any further additive unnecessary.

There is not yet a satisfactory agent for topical treatment of nail disorders caused by mycoses (fungi), which is used either without an additional carrier or without an additional active substance. The C1-C4 alkyl esters of lactic acid, malic acid, tartaric acid and also citric acid show surprisingly good antimycotic effects and at the same time good properties as carriers themselves, which guarantee the required quantity of active substance for a lasting therapeutic effect as cosmetic agents for topical treatment of nail disorders, i.e. the transport of a C1-C4 alkyl ester of the corresponding acids through the nail into the underlying nail bed and root (matrix).

The C1-C4 alkyl esters to be used as active substance and carrier at the same time comprise the methyl, ethyl, n-propyl, isopropyl, n-butyl, sec-butyl, isobutyl and tert-butyl esters. Among the esters of the polybasic acids malic acid, citric acid and tartaric acid, the C1-C4 alkyl groups contained in the ester groups may be the same or different. In the aforementioned polybasic acids, all carboxy groups or part of the carboxy groups may be esterified. Apart from malic and tartaric acid C1-C4 alkyl esters, therefore, the corresponding malic and tartaric acid C1-C4 dialkyl esters and the corresponding malic and tartaric acid monoalkyl esters may also be considered.

Of the C1-C4 alkyl esters of citric acid, the corresponding monoalkyl, dialkyl and trialkyl esters are suitable.

Preferred esters are the ethyl esters. Further preferred esters are the isopropyl esters.

A preferred single compound is ethyl lactate. Further preferred single compounds are diethyl malate and disopropyl malate. Likewise monoethyl tartrate and monoethyl citrate are described as preferred compounds.

Besides one or more C1-C4 alkyl esters of lactic acid, malic acid, tartaric acid or citric acid, agents for topical application according to the invention may comprise customary physiologically acceptable excipients.

Suitable excipients of this type are, for example, terpenes or oils containing terpenes, alcohols, ketones, fatty acid esters, polyglycols, tensides, urea, antioxidants and complexing agents.

Suitable terpenes are acyclic, monocyclic and bicyclic terpenes and also oils which contain these terpenes. Examples of acyclic terpenes are acyclic terpene hydrocarbons, such as e.g. myrcene, acyclic terpene alcohols, such as e.g. citronellol and geraniol, as well as acyclic terpene aldehydes and ketones, such as e.g. citral, α-ionone and β-ionone. Examples of monocyclic terpenes are monocyclic terpene hydrocarbons, such as e.g. α-terpenes, γ-terpenes and limonenes, monocyclic terpene alcohols, such as e.g. thymol, menthol, cineol and carvacrol, as well as monocyclic terpene ketones, such as e.g. menthone and carvone.

Examples of bicyclic terpenes are terpenes from the carane group, such as e.g. carone, terpenes from the pinane group, such as e.g. α-pinene and β-pinene, and also terpenes from the bornane group, such as e.g. campher and borneol. Especially suitable terpenes are monocyclic terpene alcohols, such as e.g. thymol and menthol. Examples of suitable oils containing terpenes are peppermint oil, cardamom oil, geranium oil, rose oil, thuja oil and thyme oil. Especially suitable oils are peppermint oil, lavender oil, tea tree oil, ABC oil (callitris intratropica wood oil) and thyme oil.

Suitable alcohols are branched or unbranched alcohols with 1 to 3 hydroxy groups and 2 to 6 carbon atoms, wherein the hydroxyl groups may be partially or fully etherified and esterified. Especially suitable alcohols are ethanol, 1-propanol, 2-propanol (isopropanol), 1,2-propandiol (propylene glycol), 2-phenylethanol (phenyl ethyl alcohol), 1-butanol (butyl alcohol), ethylene glycol monomethyl ether (methoxyethanol), ethylene glycol monophenyl ether (phenoxyethanol), 1,2,3-trihydroxypropane (glycerol), ethyl acetate, butyl acetate, glycerol diacetate (diacetine) and glycerol triacetate (triacetin).

Suitable ketones that may be considered are, for example, acetone and methyl ethyl ketone (2-butanone).

Esters of saturated and unsaturated, branched and unbranched fatty acids with 8 to 21 carbon atoms, wherein the alcohol component comprises branched and unbranched alcohols with 1 to 6 carbon atoms, are suitable as fatty acid esters. Especially suitable fatty acid esters are tridecanecarboxylic acid isopropyl ester, tetradecanecarboxylic acid isopropyl ester (isopropyl myristate), pentadecanecarboxylic acid methyl ester and 9-octadecenoic acid glycerol monoester (glycerol monooleate).

A suitable polyglycol, for example, is polyglycol 400.

Suitable tensides, for example, are non-ionogenic surfactants. Especially suitable tensides are partial fatty acid esters of sorbitan (Span), partial fatty acid esters of polyoxyethylene sorbitan (Tween), fatty acid esters of polyoxyethylene (Myrj) and fatty alcohol ethers of polyoxyethylene (Brij).

Suitable antioxidants, for example, are butyl hydroxyl toluene (BHT), butyl-4-methoxy-phenol (BHA), tocopherols and ascorbates.

Suitable complexing agents, for example, are ethylenediaminetetraacetic acid (EDTA) and disodium ethylenediaminetetraacetic acid ($Na_2$-ETDA).

Formulations for topical application according to the invention which could be considered suitable are, for example, anhydrous solutions, tinctures, emulsions, gels, ointments, creams and pastes. Preferred topical dosage forms are anhydrous solutions. The solution obtained is preferably used directly as such for topical application.

However, the anhydrous solution obtained may also be produced in another topical dosage form with the addition of further physiologically acceptable formulation aids using conventional methods of dissolution, blending and suspension.

The agents for topical use according to the invention are preferably used in the form of anhydrous solutions.

Preferred agents for topical use comprise according to this invention 1 to 99.9% by weight of one or more C1-C4 alkyl esters of lactic acid, malic acid, tartaric acid or citric acid and 0 to 98.99% by weight of one or more physiologically acceptable excipients.

As mentioned in the introduction, the invention relates to the use of agents for topical use according to the invention for the treatment, prevention, follow-up or supportive treatment of nail disorders and periungual diseases and for nail care. In particular, the invention relates to the treatment of fungal infections, for example finger or toe-nails infected with *Candida albicans* or *Trichophyton mentagroph*. Furthermore, agents according to the invention may also be used for the treatment of fungal infections of hooves, claws and talons of pets and farm animals and wild animals living in captivity.

Agents which are typically intended for topical use and comprise a C1-C4 alkyl ester of said acids are suitable as antimycotic agents, for example, for
 treatment, prevention and follow-up treatment of onychomycosis caused by dermatophytes, yeasts or moulds or mixed infections,
 treatment, prevention and follow-up treatment of fungal infections of the nails in patients with psoriasis, diabetes or also AIDS,
 supportive therapy for periungual nail infections such as e.g. *Candida paronychium, Candida albicans* or *Trychophyton mentagroph.*

As already mentioned, pharmaceutical agents according to the invention are suitable for the treatment of nail disorders and periungual diseases of toe and finger nails, and also for the treatment of hooves, claws and talons of pets and farm animals and wild animals in captivity (zoo). The frequency of application of the agent according to the invention depends on the extent and localization of the disorders.

Generally, one to three applications daily are sufficient.

The anhydrous solution in this case is applied directly to the diseased nail, or hoof, claw or talon, and if necessary also to the likewise infected surrounding areas of skin using a pipette or applicator.

The agents for topical use according to the invention have the advantage that they penetrate the diseased nail and can exert the full effect in the nail bed or nail root within a few days.

EXAMPLE 1

Nail Applicator Comprising
Lactic acid ethyl ester, pure without additives.

EXAMPLE 2

| Nail applicator comprising | |
|---|---|
| Malic acid diethyl ester | 70% |
| Ethanol | 30%, |
| No further additives. | |

EXAMPLE 3

| Nail applicator comprising | |
|---|---|
| Citric acid triethyl ester | 50% |
| Isopropanol | 50%. |
| No further additives. | |

EXAMPLE 4

| Nail applicator comprising | |
|---|---|
| Tartaric acid diethyl ester | 40% |
| Ethanol | 30% |
| Propylene glycol | 30% |
| No further additives. | |

The following, for example, may be used as possible applicators:

1) Applicators based on a capillary system, comparable with textile liners, which are made of suitably resistant materials such as e.g. polypropylene, described in DE 3202435C1 and U.S. Pat. No. 4,973,181.
2) Swab bottles with automatic spring or roll closure such as e.g. Dab-O-Matic from Dab-O-Matic Corp. in Mount Vernon, N.Y. (USA), or
3) Customary tincture bottles of glass or plastic with a brush or pipette built into the cap.

The invention claimed is:

1. A method for the treatment of nail disorders and periungual diseases caused by mycoses, comprising topically applying a water-free topical application composition to a subject in need thereof,
wherein the water-free topical application composition consists essentially of one or more C1-C4 alkyl ester of lactic acid, malic acid, tartaric acid or citric acid as the sole active ingredient and
optionally, one or more physiologically acceptable excipients.

2. The method according to claim 1, wherein the one or more C1-C4 alkyl esters is an ethyl ester of lactic acid, malic acid, tartaric acid or citric acid.

3. The method according to claim 1, wherein the one or more C1-C4 alkyl esters is an isopropyl ester of lactic acid, malic acid, tartaric acid or citric acid.

4. The method according to claim 1, wherein the one or more C1-C4 alkyl esters is lactic acid ethyl ester.

5. The method according to claim 1, wherein the one or more C1-C4 alkyl esters is malic acid diisopropyl ester.

6. The method according to claim 1, wherein the water-free topical application composition consists essentially of 1 to 99.99% by weight of C1-C4 alkyl esters of lactic acid, malic acid, tartaric acid or citric acid.

7. The method according to claim 1 for treatment of fungal infections of hooves, claws and talons of pets and farm animals and wild animals living in captivity.

8. The method according to claim 1, wherein the one or more physiologically acceptable excipients are selected from the group consisting of terpenes or oils containing terpenes, alcohols, ketones, fatty acid esters, polyglycols, tensides, urea, antioxidants and complexing agents.

9. The method according to claim 1, wherein the water-free topical application composition consists essentially of 30 to 98.99% by weight of the one or more physiologically acceptable excipients.

10. The method according to claim 1, wherein the one or more C1-C4 alkyl esters of lactic acid, malic acid, tartaric acid or citric acid is/are present in the composition in an amount effective to kill *Candida albicans* and/or *Trichophyton mentagroph*.

* * * * *